United States Patent
Analytis et al.

(10) Patent No.: US 11,433,166 B2
(45) Date of Patent: Sep. 6, 2022

(54) LIQUID LEVEL SENSOR FOR LIQUID RECEPTACLE

(71) Applicant: Moxxly LLC, Wilmington, DE (US)

(72) Inventors: Santhi Analytis, San Francisco, CA (US); Wisit Jirattigalachote, San Francisco, CA (US); Jacob Kurzrock, San Francisco, CA (US); Gabrielle Guthrie, San Francisco, CA (US); Jose Luis Cordoba, Malaga (ES)

(73) Assignee: Moxxly LLC, Wilmington, DE (US)

( * ) Notice: Subject to any disclaimer, the term of this patent is extended or adjusted under 35 U.S.C. 154(b) by 582 days.

(21) Appl. No.: 16/398,028

(22) Filed: Apr. 29, 2019

(65) Prior Publication Data
US 2019/0328945 A1    Oct. 31, 2019

Related U.S. Application Data

(60) Provisional application No. 62/663,719, filed on Apr. 27, 2018.

(51) Int. Cl.
*A61M 1/06* (2006.01)
*A61M 39/24* (2006.01)
*G01F 23/14* (2006.01)
*A61M 39/10* (2006.01)

(52) U.S. Cl.
CPC ............ *A61M 1/062* (2014.02); *A61M 39/24* (2013.01); *G01F 23/14* (2013.01); *A61J 2200/76* (2013.01); *A61M 2039/1077* (2013.01); *A61M 2205/3331* (2013.01); *A61M 2205/3389* (2013.01); *A61M 2205/3393* (2013.01)

(58) Field of Classification Search
CPC ...... A61J 2200/76; A61M 1/062; G01F 23/14
See application file for complete search history.

(56) References Cited

U.S. PATENT DOCUMENTS

| | | | | |
|---|---|---|---|---|
| 4,531,405 | A  * | 7/1985 | Leister | G01F 23/14 |
| | | | | 73/290 R |
| 2004/0231414 | A1* | 11/2004 | Delnevo | A61M 1/3624 |
| | | | | 73/290 R |
| 2014/0033817 | A1* | 2/2014 | Scheldorf | G01F 23/164 |
| | | | | 73/299 |
| 2014/0236072 | A1* | 8/2014 | Zhang | A61M 13/003 |
| | | | | 604/23 |
| 2015/0198475 | A1* | 7/2015 | Vander Horst | G01F 23/165 |
| | | | | 73/302 |
| 2016/0310657 | A1* | 10/2016 | Solem | A61M 1/3627 |
| 2017/0097254 | A1* | 4/2017 | Smith | G01F 23/14 |
| 2017/0303496 | A1* | 10/2017 | Fematt | G01F 23/24 |
| 2018/0001001 | A1* | 1/2018 | Wu | A61M 1/064 |
| 2018/0264491 | A1* | 9/2018 | Goldowsky | B01L 3/0293 |
| 2018/0361040 | A1* | 12/2018 | O'Toole | A61M 1/066 |
| 2018/0369464 | A1* | 12/2018 | Aalders | A61M 1/73 |

\* cited by examiner

*Primary Examiner* — Jenna Zhang
(74) *Attorney, Agent, or Firm* — Loyal IP Law, PLLC; Travis Banta

(57) ABSTRACT

Disclosed herein are various techniques and devices for detecting a level of fluid within a fluid collection receptacle. In one embodiment, a pressure sensor connected to a bottle is provided. The pressure sensor detects air pressure in the bottle as the bottle is filled with a liquid and provides information to determine a volume of the liquid in the bottle.

13 Claims, 18 Drawing Sheets

*1500*

LIQUID LEVEL SENSOR FOR LIQUID RECEPTACLE

CROSS-REFERENCE TO RELATED APPLICATIONS

This application claims the benefit of U.S. Provisional Application No. 62/663,719, filed Apr. 27, 2018, which is incorporated herein by reference in its entirety, including but not limited to those portions that specifically appear hereinafter, the incorporation by reference being made with the following exception: In the event that any portion of the above-referenced provisional application is inconsistent with this application, this application supersedes said above-referenced provisional application.

BACKGROUND

1. Technical Field

This disclosure relates generally to a liquid level sensor for detecting an amount of liquid in a liquid receptacle. In one embodiment, a liquid level sensor may obtain sensor data by detecting a level of milk in a milk bottle and using that sensor data to determine an amount of milk or volume of milk within the bottle. Sensors may be disposed within the receptacle and continuously monitor a liquid level within the receptacle and provide updated sensor data reflecting an increased liquid level.

2. Description of the Related Art

Receptacles for fluid storage and collection have existed since antiquity. More recently, some receptacles have been marked with graduated measurement indicators. Beakers, metal jars, measuring cups, pitchers, and a host of other fluid storage and collection receptacles have been marked with graduated measurement indicators to show how much fluid is contained within the receptacle. The graduated measurement indicators may be marked on the fluid storage and collection receptacles based on mathematical volumetric calculations to accurately reflect an amount of fluid within the fluid storage and collection receptacles. In other words, various indicators may be marked on the side of a fluid storage and collection receptacle to accurately measure a fluid level within the receptacle. For example, the receptacle may include indicators that show one ounce, two ounces, three ounces, etc., which when compared to a fluid level within the receptacle shows a person how much liquid, in fluidic measurements, is contained within the receptacle.

While these graduated indicators are helpful, their usefulness is somewhat limited. For example, in fluid collection receptacles, graduated indicators provide no indication of flow rate, e.g., how much fluid is collected per time unit. In situations where fluid collection is a slow process, a person may lose interest or be unable to monitor a flow rate due to the amount of time necessary to obtain a flow rate. Another weakness of graduated indicators is that graduated indicators are only helpful if the receptacle is in an area where it can be easily seen by a person. Thus, in applications where the fluid collection receptacle is hidden or not readily visually accessible, graduated indicators provide a person with no useful information about the volume of liquid collected within the collection receptacle.

One specific situation where graduated indicators are of limited usefulness is in nursing an infant or breast pumping. Typical breast pumps include a bottle that collects milk as it is pumped. However, in many situations, it may be inconvenient for a mother to access a bottle during pumping. For example, since a bottle is usually connected to a breast pump which is, in turn, connected to the mother's breast, it may be difficult for a mother to accurately see how much milk has been collected within the milk receptacle. Similarly, when a mother is pumping from both breasts, it may be difficult for a mother to accurately assess how much milk has been produced over a certain amount of time from each breast using nothing more than graduated indicators and a stop watch.

It is therefore one object of this disclosure to provide a flow rate sensor system and apparatus. It is a further object of this disclosure to provide a fluid receptacle that includes one or more sensors installed within the receptacle. Another object of this disclosure is to provide a sensor to sense a fluid level within a fluid receptacle and to sense a flow rate for fluid entering the receptacle. Another object of this disclosure is to provide a fluid receptacle which contains one or more sensors to accurately sense a fluid level within the fluid receptacle and sense a flow rate for milk entering the receptacle.

SUMMARY

Disclosed herein is a pressure sensor connected to a bottle. The pressure sensor detects air pressure in the bottle as the bottle is filled with a liquid and provides information to determine a volume of the liquid in the bottle.

BRIEF DESCRIPTION OF THE DRAWINGS

The accompanying drawings illustrate one or more embodiments of a fluid collection receptacle within which is installed one or more sensors for accurately assessing both a flow rate and amount of milk contained within the fluid collection receptacle.

DETAILED DESCRIPTION OF PREFERRED EMBODIMENTS

In the following description, for purposes of explanation and not limitation, specific techniques and embodiments are set forth, such as particular techniques and configurations, in order to provide a thorough understanding of the device disclosed herein. While the techniques and embodiments will primarily be described in context with the accompanying drawings, those skilled in the art will further appreciate that the techniques and embodiments may also be practiced in other similar devices.

Reference will now be made in detail to the exemplary embodiments, examples of which are illustrated in the accompanying drawings. Wherever possible, the same reference numbers are used throughout the drawings to refer to the same or like parts. It is further noted that elements disclosed with respect to particular embodiments are not restricted to only those embodiments in which they are described. For example, an element described in reference to one embodiment or figure, may be alternatively included in another embodiment or figure regardless of whether or not those elements are shown or described in another embodiment or figure. In other words, elements in the figures may be interchangeable between various embodiments disclosed herein, whether shown or not.

Figure 1:
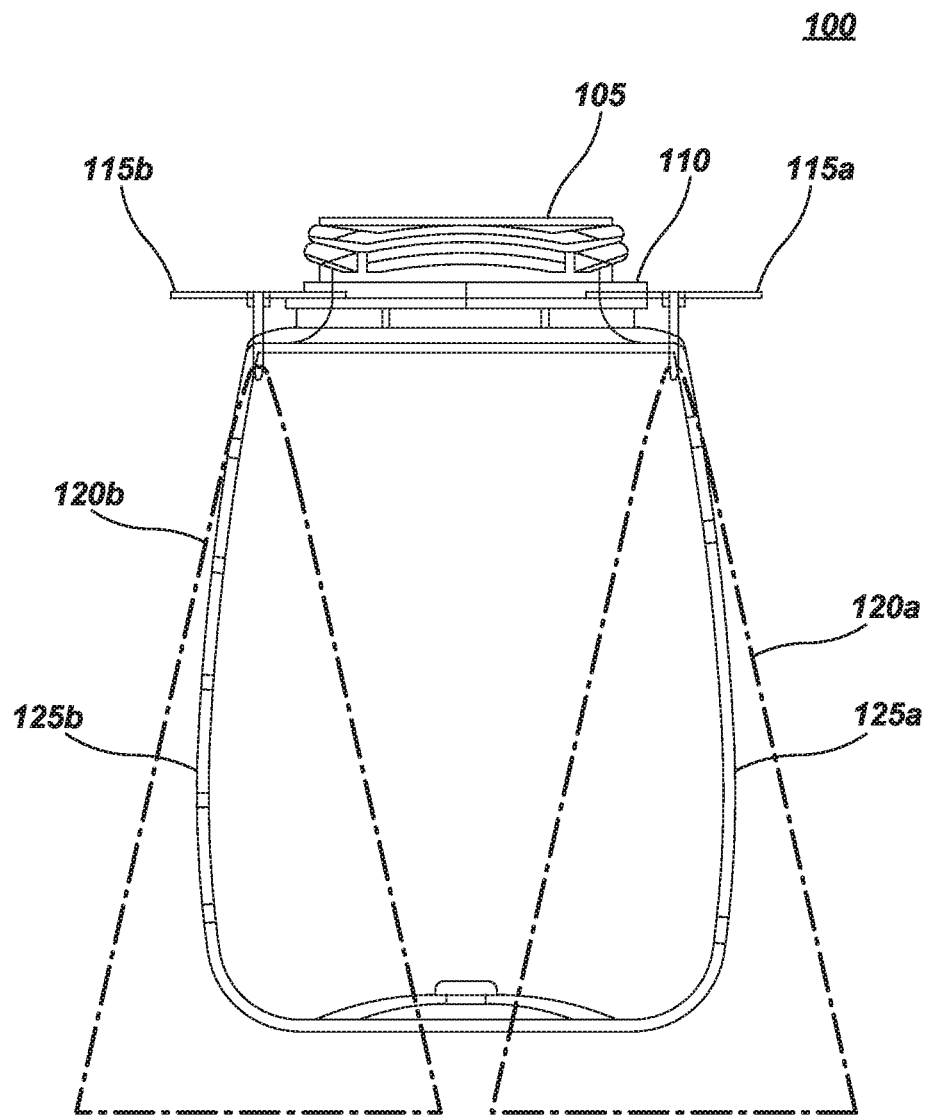
FIG. 1 illustrates a fluid collection receptacle including one or more sensors.

FIG. 1 illustrates a fluid collection receptacle 100 including one or more of sensor 115a and sensor 115b. Fluid collection receptacle 100 may be implemented as a bottle for collecting milk via a breast pump. In one embodiment, milk may be collected within fluid collection receptacle 100 via opening 105. Opening 105 of fluid collection receptacle 100 may be encompassed by a collar 110 which allows fluid collection receptacle 100 to mate with or screw into another element, such as a breast pump. Fluid collection receptacle 100 includes one or more sensors, such as sensor 115a and sensor 115b. Sensor 115a may be implemented singly or in combination with sensor 115b and vice versa. Sensor 115a and/or sensor 115b may be disposed along collar 110 of fluid collection receptacle 100, as shown in FIG. 1. However, sensor 115a and sensor 115b may be positioned along a top portion of fluid collection receptacle 100. More specifically, sensor 115a and sensor 115b may be positioned anywhere fluid collection receptacle side 125a or fluid collection receptacle side 125b meet collar 110.

Sensor 115a being positioned along or about collar 110 provides a field-of-view for sensor 115a of fluid collection receptacle side 125a within sensing cone 120a. Similarly, sensor 115b being positioned along or about collar 110 provides a field-of-view for sensor 115b of fluid collection receptacle side 125b within sensing cone 120b. Sensor 115a and/or sensor 115b, depending on specific configuration, may emit a beam of light substantially parallel to fluid collection receptacle side 125a and/or fluid collection receptacle side 125b, respectively. Sensor 115a may further receive a reflection of a beam of light within sensing cone 120a. Similarly, sensor 115b may receive a reflection of a beam of light within sensing cone 120b.

Sensor 115a and sensor 115b may be implemented as "time-of-flight" sensors. In other words, sensor 115a and sensor 115b may be used to determine an amount of time between when a beam of light is emitted and when a reflection of the beam of light is detected. By simple calculation using the known constant for the speed of light, a computer processor associated with sensor 115a and sensor 115b may determine a distance between sensor 115a and sensor 115b and a level of liquid collected within fluid collection receptacle 100. Accordingly, as liquid collects within fluid collection receptacle 100 sensor 115a and sensor 115b may constantly monitor a level of rising fluid within fluid collection receptacle 100. For example, as milk is collected during a breast pumping session, sensor 115a and sensor 115b may be used to determine a liquid level of milk contained within fluid collection receptacle 100 by a computer processor associated with sensor 115a and sensor 115b. Further, the computer processor associated with sensor 115a and sensor 115b may use a known volume of fluid collection receptacle 100 to calculate flow rate for liquid entering fluid collection receptacle 100 and a volume of liquid contained within fluid collection receptacle 100.

In some situations, sensor 115a may be adequate to determine a liquid level of fluid contained within fluid collection receptacle 100. However, sensor 115b may be useful in other situations, such as when fluid collection receptacle 100 is not level or a surface of the fluid contained within fluid collection receptacle 100 is not horizontal. To ensure accurate measurement of a liquid level, a volume, a flow rate, or other measurement, fluid collection receptacle 100 may, in some situations, be implemented with an accelerometer to measure tilt angles.

Figure 2:
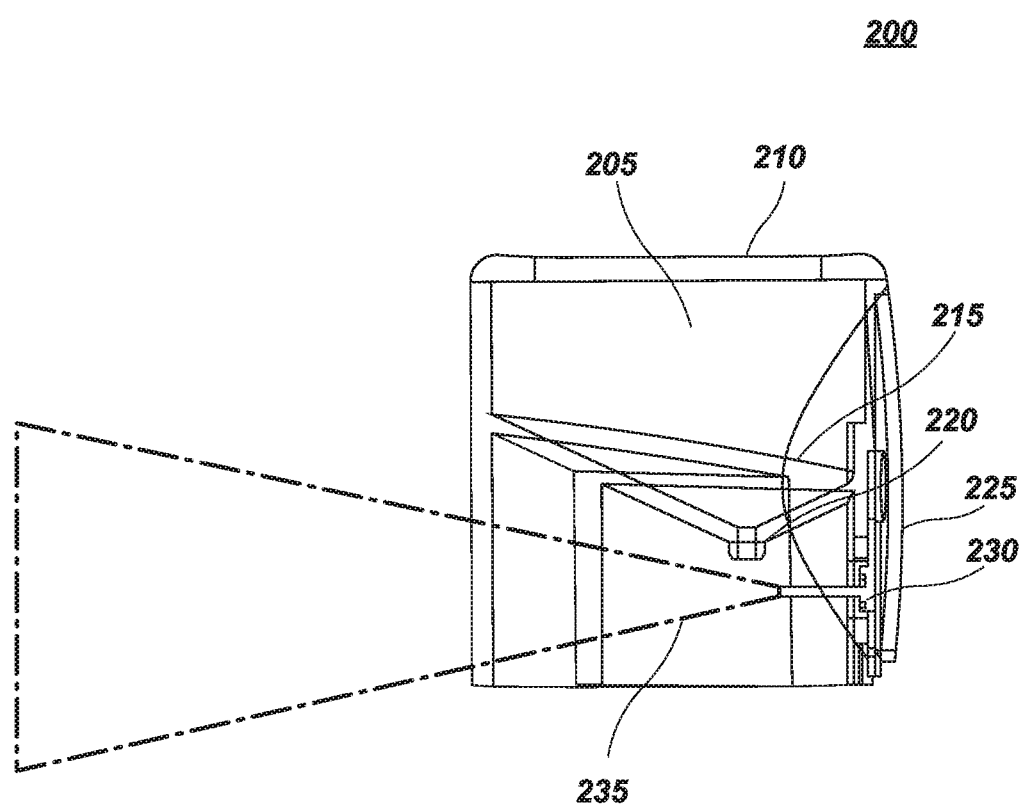
FIG. 2 illustrates a top for a fluid collection receptacle including a sensor.

FIG. 2 illustrates a top 200 for a fluid collection receptacle, such as fluid collection receptacle 100 shown in FIG. 1, including a sensor 230, as will be discussed below. Fluid collection receptacle 100, for example, may connect with top 200 which, in turn, may connect to other elements of a breast pump. Top 200 may be disposed in a housing 205 which may be generally cylindrical. It is noted that housing 205 may be implemented in any sufficient shape. Housing 205 includes an opening 210 through which milk, for example, may drain from a breast pump into housing 205. The milk, in this example, may land on an inclined plane 215 which funnels milk to a spout 220. Spout 220 meters milk into droplets of substantially uniform size.

Housing 205 may further include a side portion 225 in which a sensor 230 is disposed. Sensor 230 may also be implemented as a time-of-flight sensor which includes a field-of-view of the milk droplets released from spout 220 through sensing cone 235 of sensor 230. As droplets are released from spout 220 and pass through sensing cone 235, sensor 230 may detect a number of uniform droplets and calculate an overall volume for milk that has been released from spout 220. One advantage of top 200 is that regardless of an angle of tilt of top 200, up to approximately 45°, a droplet of milk released from spout 220 will pass through sensing cone 235 of sensor 230. In this manner, an accurate measurement of a volume of liquid collected within a fluid collection receptacle, such as fluid collection receptacle 100 shown in FIG. 1, may be determined.

Figure 3:
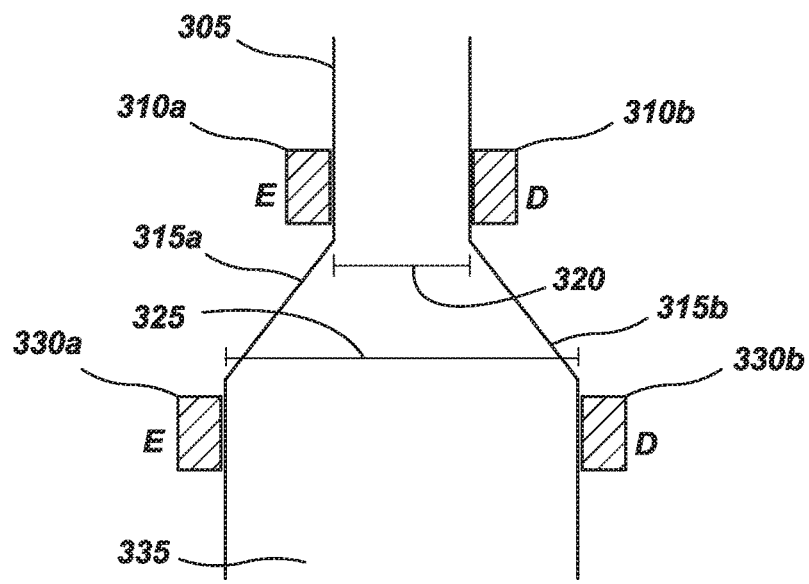
FIG. 3 illustrates a sensor configuration for a fluid collection receptacle which avoids false readings due to fluid droplets running down an inside portion of the fluid collection receptacle.

FIG. 3 illustrates a sensor configuration for a fluid collection receptacle 300 that avoids false readings due to fluid droplets running down an inside portion of fluid collection receptacle 300. Fluid collection receptacle 300 may include an opening 305 through which milk is drained from a breast pump. In some circumstances, milk that is drained from the breast pump may flow down a side of opening 305 which may result in a quantity of milk not being accurately detected between emitter 310a and detector 310b. Accordingly, as shown in FIG. 3, opening 305 may be expanded outwardly along fluid collection receptacle edges 315a and 315b. This outward expansion of opening 305 along edges 315a and 315b increases a first diameter 320 of opening 305 to a second diameter 325 where the first diameter 320 is less than the second diameter 325. In other words, because of the outward expansion of edges 315a and 315b, a milk droplet stuck to the side of opening 305 must drop when the milk droplet encounters edges 315a and 315b.

Accordingly, any milk that has been drained through opening 305 from the breast pump may be formed in droplets by at least a top of edges 315a and 315b. In this manner, droplets may be detected between emitter 330a and detector 330b as the droplets fall into a collection portion 335 of fluid collection receptacle 300. In one embodiment, a computer processor associated with the breast pump may compare the number of droplets detected between emitter 310a and detector 310b with the number of droplets detected between emitter 330a and detector 330b to determine an overall flow rate of milk, or other fluid, as the milk is collected within collection portion 335 of fluid collection receptacle 300.

Figure 4:
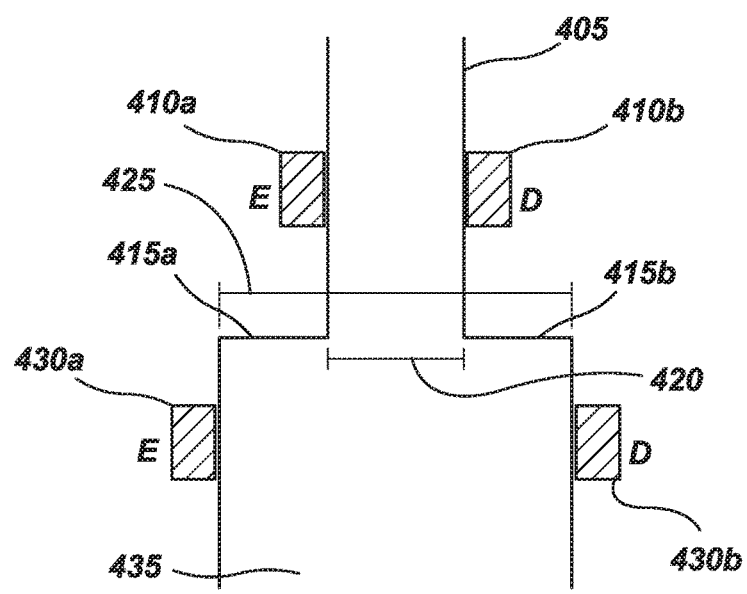
FIG. 4 illustrates an alternative sensor configuration for a fluid collection receptacle which avoids false readings due to fluid droplets running down an inside portion of the fluid collection receptacle.

FIG. 4 illustrates an alternative sensor configuration for a fluid collection receptacle 400 that avoids false readings due to fluid droplets running down an inside portion of the fluid collection receptacle. Fluid collection receptacle 400 may include an opening 405 through which milk is drained from a breast pump. In some circumstances, milk that is drained from the breast pump may drain down a side of opening 405 which may result in a quantity of milk not being accurately detected between emitter 410a and detector 410b. Accordingly, as shown in FIG. 4, opening 405 may be expanded outwardly, at right angles to opening 405 by collection receptacle edges 415a and 415b creating a defined break between opening 405 and collection portion 435 of fluid collection receptacle 400. This outward expansion of opening 405 along edges 415a and 415b increases a first diameter 420 of opening 405 to a second diameter 425 where the first diameter 420 is less than the second diameter 425. In other words, because of the outward expansion of edges 415a and 415b, a milk droplet stuck to the side of opening 405 must drop when the milk droplet encounters edges 415a and 415b.

Accordingly, any milk that has been drained through opening 405 from the breast pump may be formed in droplets by at least a top of edges 415a and 415b. In this manner, droplets may be detected between emitter 430a and detector 430b as the droplets fall into a collection portion 435 of fluid collection receptacle 400. In one embodiment, a computer processor associated with the breast pump may compare a number of droplets detected between emitter 410a and detector 410b with a number of droplets detected between emitter 430a and detector 430b to determine an overall flow rate of milk, or other fluid, as the milk is collected within collection portion 435 of fluid collection receptacle 400.

Figure 5A:
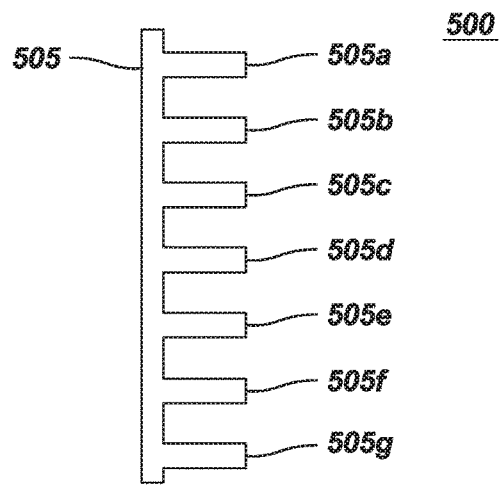
FIG. 5a illustrates a sensor which may be installed within a fluid collection receptacle.

FIG. 5A illustrates a sensor 500 which may be installed within a fluid collection receptacle. Sensor 500 operates as a capacitive sensor. For example, the capacitance of sensor 500 may be proportional due to dielectric variation caused by a changing volume of liquid inside a container, such as a fluid collection receptacle. In this manner sensor 500 may be installed within a portion of a fluid collection receptacle, such as those disclosed herein. Sensor 500 may be disposed on an inside surface of a fluid collection receptacle, may be disposed within a wall of a fluid collection receptacle, or may be disposed on an outside surface of a fluid collection receptacle.

As shown in FIG. 5A, sensor 500 includes a conductive trace 505 which connects fingers 505a-505g. Finger 505g may be disposed at a bottom of a fluid collection receptacle while finger 505a may be disposed at a top of a fluid collection receptacle. As a fluid, such as milk, is collected within a fluid collection receptacle the level of milk proceeds up from finger 505g towards finger 505a. Further, as the fluid level increases, or raises, within a fluid collection receptacle a capacitance within sensor 500 changes proportionally to the increase of the fluid level. A computer processor associated with a breast pump may detect these proportional changes in the capacitance of sensor 500 as a level of fluid increases within the fluid collection receptacle. The capacitance may be detected and correlated with an overall volume of fluid contained within the fluid collection receptacle.

Figure 5B:
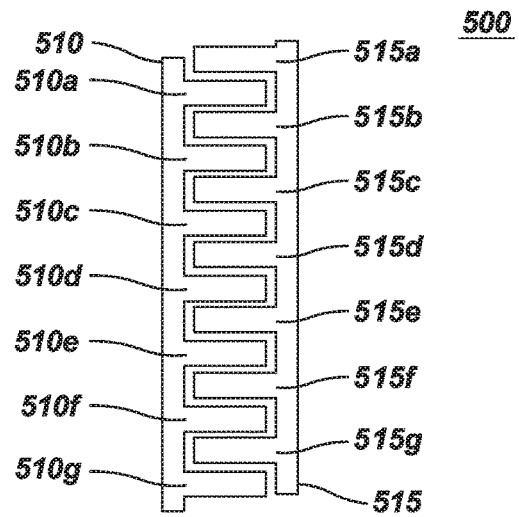
FIG. 5b illustrates another sensor which may be installed within a fluid collection receptacle.

FIG. 5B illustrates a sensor 500 which may be installed within a fluid collection receptacle. In FIG. 5B, sensor 500 is implemented in a symmetric interlaced fashion. As before with respect to FIG. 5A, a conductive trace 510 is connected to a plurality of fingers 510a-510g. To increase capacitive resolution and minimize crosstalk between fingers 505a-505g shown in FIG. 5A, a second conductive trace 515 is provided with fingers 515a-515g which are installed in the fluid collection receptacle. In this embodiment, for example, finger 510a is separated from finger 510b by finger 515b, and so on providing an interlaced relation between fingers 510a-510g and fingers 515a-515g, as shown in FIG. 5B.

Figure 5C:
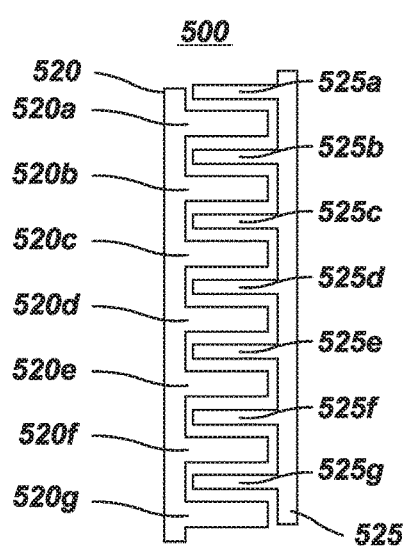
FIG. 5c illustrates another sensor which may be installed within a fluid collection receptacle.

FIG. 5C illustrates a sensor 500 which may be installed within a fluid collection receptacle. In FIG. 5C, sensor 500 is implemented in an asymmetric interlaced fashion. As before with respect to FIG. 5B, a conductive trace 520 includes fingers 520a-520e while conductive trace 525 includes fingers 525a-525e. However, fingers 525a-525e are narrower in terms of width than fingers 520a-520e to provide a desired capacitive resolution. In other words, fingers 520a-520e individually occupy a greater area than any one of fingers 525a-525e. Variations in total area between sets of fingers 520a-520e and fingers 525a-525e adjust a relative amount of capacitance within sensor 500 which, in turn, adjusts a resolution of sensor 500 to accurately detect a fluid level within a fluid collection receptacle.

Figure 5D:
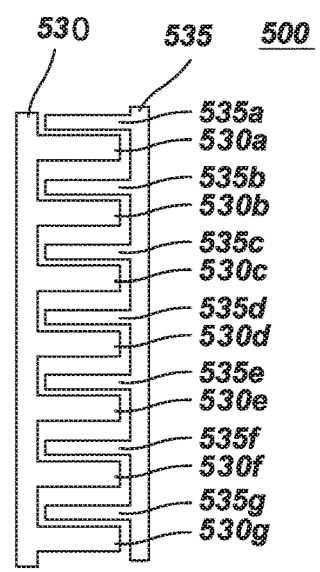
FIG. 5d illustrates another sensor which may be installed within a fluid collection receptacle.

FIG. 5D illustrates a sensor 500 to be installed within a fluid collection receptacle. Sensor 500 of FIG. 5D is an alternative example of an offset or skewed asymmetric interlaced sensor. Sensor 500 includes a conductive trace 530 which is connected to fingers 530a-530g and a conductive trace 535 which is connected to fingers 535a-535f. Fingers 535a-535f, however, not only have a smaller area than fingers 530a-530g but also are skewed closer to a finger below than to a finger above a particular finger. In other words, finger 535a is skewed closer to finger 530a, while finger 535b is skewed closer to finger 530b, and so on. Skewing distances between fingers 530a-530g and fingers 535a-535f adjusts a relative amount of capacitance between fingers 530a-530g and fingers 535a-535f in sensor 500 which, in turn, adjusts the resolution of sensor 500 to accurately detect a fluid level within a fluid collection receptacle using sensor 500.

Figure 6:
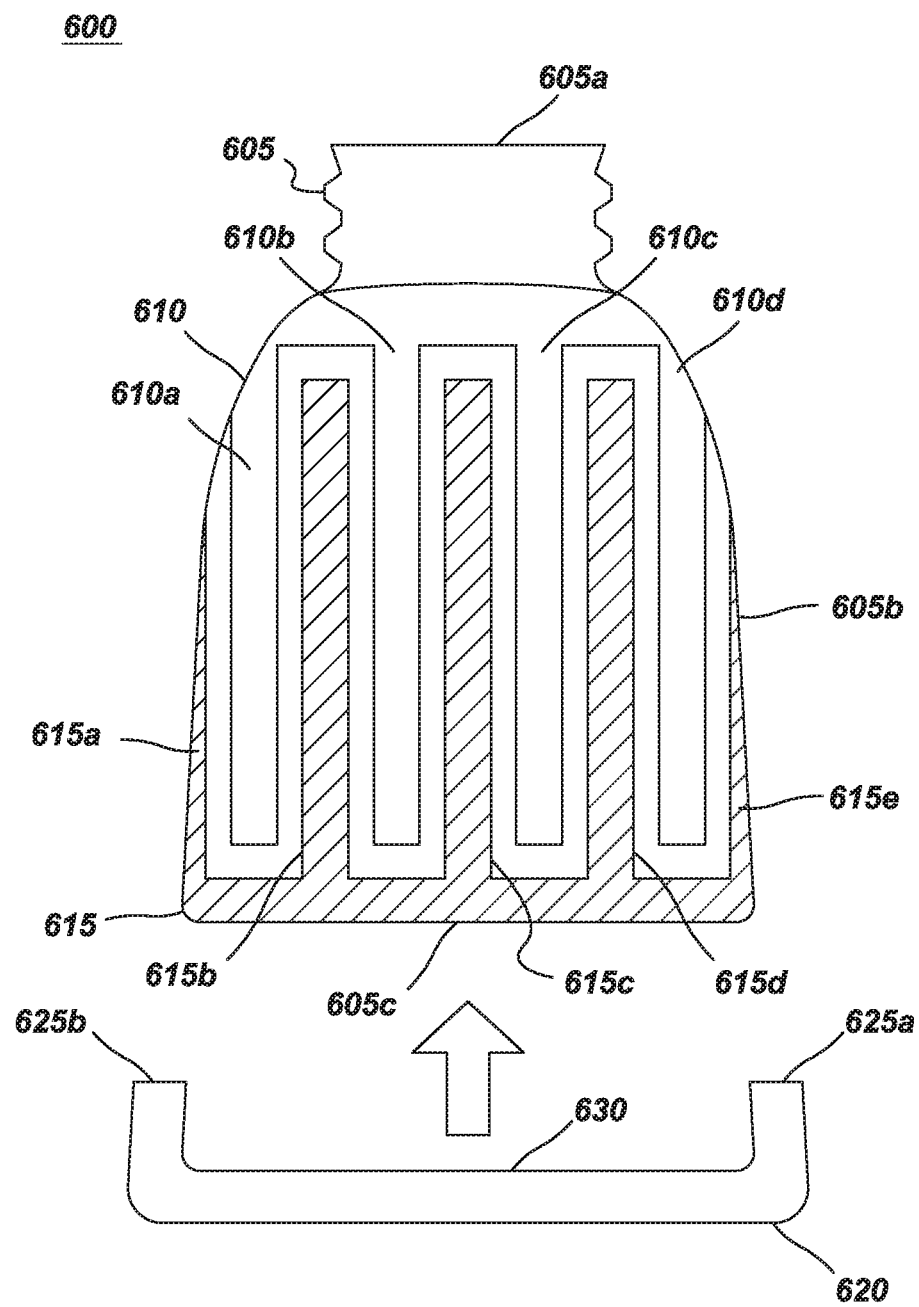
FIG. 6 illustrates a fluid collection receptacle in which sensor elements are attached to a sensor within a base portion of the fluid collection receptacle.

FIG. 6 illustrates a fluid collection receptacle 600 in which sensor element 610 and sensor element 615 are attached to a sensor 630 within a base portion 620 of fluid collection receptacle 600. Fluid collection receptacle 600 may be implemented as bottle 605. Bottle 605 includes an opening 605a through which milk, for example, may pass and be contained within bottle 605. Bottle 605 may be encompassed by a side 605b which defines a circumference of bottle 605. Bottle 605 includes, built within side 605b, a first sensor element 610 and a second sensor element 615. First sensor element 610 and second sensor element 615 are disposed within a wall of bottle 605 defined by side 605b. For example, bottle 605 may be constructed using plastic materials and first sensor element 610 and second sensor element 615 may be positioned within or contained within the plastic materials. Alternatively, first sensor element 610 and second sensor element 615 may be positioned on an inner or outer surface of side 605B.

First sensor element 610 may include one or more fingers 610a-610d while second sensor element 615 may include one or more fingers 615a-615e. First sensor element 610 may extend one or more fingers 610a-610d circumferentially down around bottle 605, as shown. Similarly, second sensor element 615 may extend one or more fingers 615a-615e circumferentially up around bottle 605. First sensor element 610 and second sensor element 615 may be implemented using any electrically conductive material. For example, first sensor element 610 and second sensor element 615 may be implemented using a metal such as copper arranged in thin sheets and cut into symmetric combs with symmetric interlacing fingers as shown in FIG. 6. In another embodiment first sensor element 610 and second sensor element 615 may be implemented using a conductive ink disposed within bottle 605 into symmetric combs with interlacing fingers as shown in FIG. 6.

Fingers 610a-610d are shown in FIG. 6 in a symmetric interlaced configuration with fingers 615a-615e. That is, for example, finger 610a is symmetrically disposed between finger 615a and finger 615b. It is noted that other configurations are possible. For example, fingers 610a-610d and 615a-615e may be implemented in an asymmetric interlaced configuration or in an offset asymmetric configuration, as discussed above. So long as fingers 610a-610d and 615a-615e are substantially equal in terms of area, mass, and density, any combination of fingers 610a-610d and 615a-615e which extends vertically along a vertical axis defined by bottle 600, first sensor element 610 and second sensor element 615 may be implemented in any configuration.

Bottle 600 may include a base portion 620 which may be attached to bottle 600 using any technique known in the art. In FIG. 6, base portion 620 is shown with attachment 625a and attachment 625b. Attachment 625a and attachment 625b are simply friction fittings that secure base portion 620 to bottle 600 by friction connection. Base portion 620 further includes a sensor 630 which electrically connects to first sensor element 610 and second sensor element 615. In this manner, sensor 630 may detect a relative amount of capacitance between first sensor element 610 and second sensor element 615. Sensor 630 may then transmit information about the relative amount of capacitance between first sensor element 610 and second sensor element 615 to a computer processor associated with the breast pump. This computer processor may, based on this information, determine a level of milk, for example, within bottle 600. The computer processor may, based on this information, further determine a volume of milk, for example, within bottle 600. The computer processor may also, based on this information, detect a flow rate for milk, for example, entering bottle 600.

Figure 7:
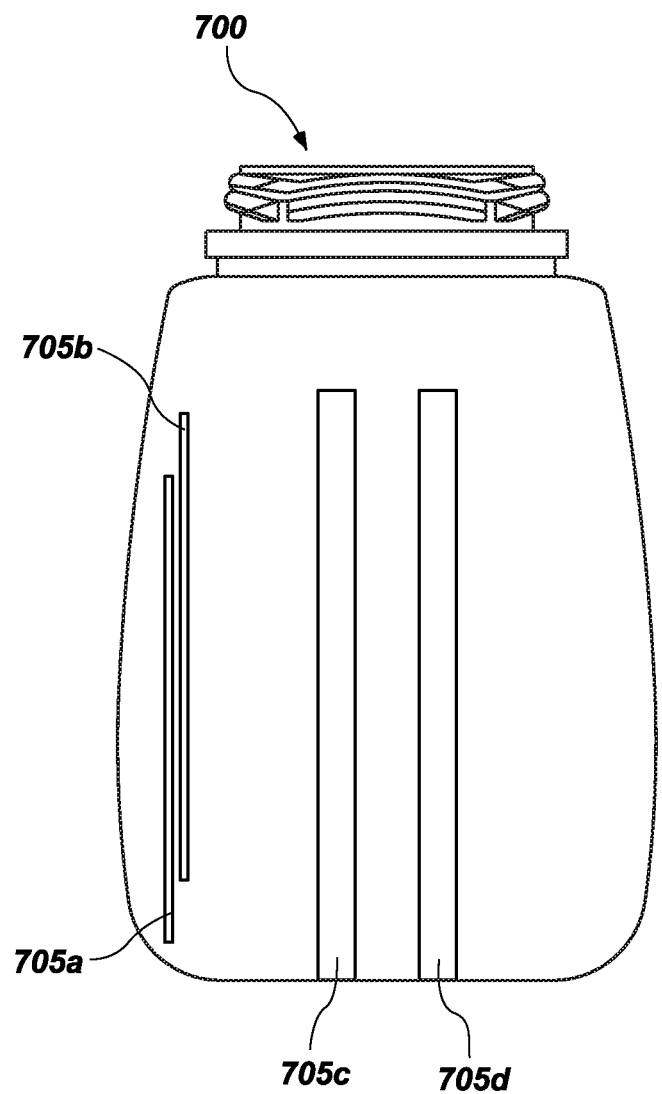
FIG. 7 illustrates a fluid collection receptacle in which sensor elements are disposed within the fluid collection receptacle.

FIG. 7 illustrates a fluid collection receptacle 700 in which sensor elements 705a-705d are disposed within fluid collection receptacle 700. In this embodiment, sensor elements 705a-705d may be silk-screened onto a surface of fluid collection receptacle 700 using conductive inks or other conductive materials. It should be noted that sensor elements 705a-705d may be installed on an outside surface of fluid collection receptacle 700, an inside surface of fluid collection receptacle 700, or between an inside and outside surface of fluid collection receptacle 700. Sensor elements 705a-705d may also be injection molded onto the bottle via comolding or overmolding of a conductive plastic material onto an insulating plastic material, for example. In another embodiment, sensor elements 705a-705d may be separable from the bottle by being installed within a sleeve that may be disposed around the outside surface of fluid collection receptacle 700.

In this manner, sensor elements 705a and 705b may be disposed on a first surface, such as a front surface, of a fluid collection receptacle 700 while sensor elements 705c and 705d may be disposed on a second surface, such as a side surface of fluid collection receptacle 700. For example, sensor elements 705a and 705b may form a first pair of sensor elements which may be disposed at approximately 90° from sensor elements 705c and 705d which may form a second pair of sensor elements. In this manner, sensor elements 705a-705d may sense an amount of fluid within fluid collection receptacle 700 even when fluid collection receptacle 700 is tilted in a left/right direction and a front/back direction.

Figure 8:
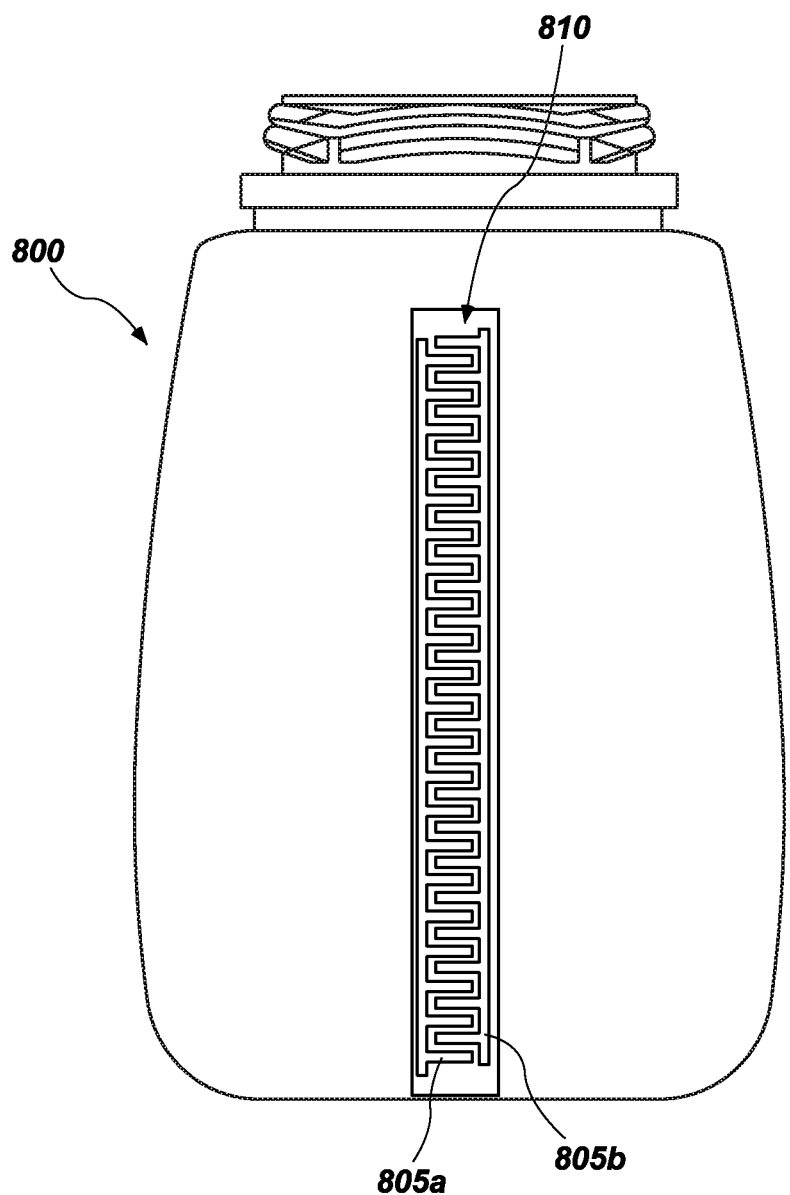
FIG. 8 illustrates a fluid collection receptacle in which sensor elements are disposed on a rod disposed within the fluid collection receptacle.

FIG. 8 illustrates a fluid collection receptacle 800 in which sensor elements 805a and 805b are disposed on a rod 810 disposed within fluid collection receptacle 800. Rod 810 may be formed to rise from a bottom portion of fluid collection receptacle 800 using the same material used for fluid collection receptacle 800 (e.g., plastic). Rod 810 may include sensor elements 805a and 805b which are similar in implementation, in this example, to sensor 500 shown in FIG. 5B using an interlaced symmetric pattern (although any of sensors 500 shown in FIGS. 5A-5D may be used on rod 810). Other shapes for sensor elements 805a and 805b are possible in any of the embodiments disclosed herein. For example, sensor elements 805a and 805b may be implemented as a series of chevrons, zig-zags, vertical lines, horizontal lines, diagonal lines, circular lines about the circumference of fluid collection receptacle 800 or other implementations. Rod 810 may or may not be hollow along an inside portion of rod 810. In this manner, sensor elements 805a and 805b may be disposed on an outside surface of rod 810, an inside surface of rod 810 or may be disposed between an inside and outside surface of rod 810 within the materials that form fluid collection receptacle 800.

In one embodiment, sensor elements 805a and 805b may be printed using conductive ink, such as silver ink, on, within, or along an inside surface of rod 810. Alternatively, sensor elements 805a and 805b may be implemented using a flexible PCB (printed circuit board) that may be fitted on, in, or outside rod 810. Fluid collection receptacle 800 may further include leads which may allow various electronic components associated with sensor elements 805a and 805b which are accessible such that electronics may be connected to sensor elements 805a and 805b while still being able to come into electrical contact with sensor elements 805a and 805b and while not coming in contact with fluid within fluid collection receptacle 800.

Figure 9:
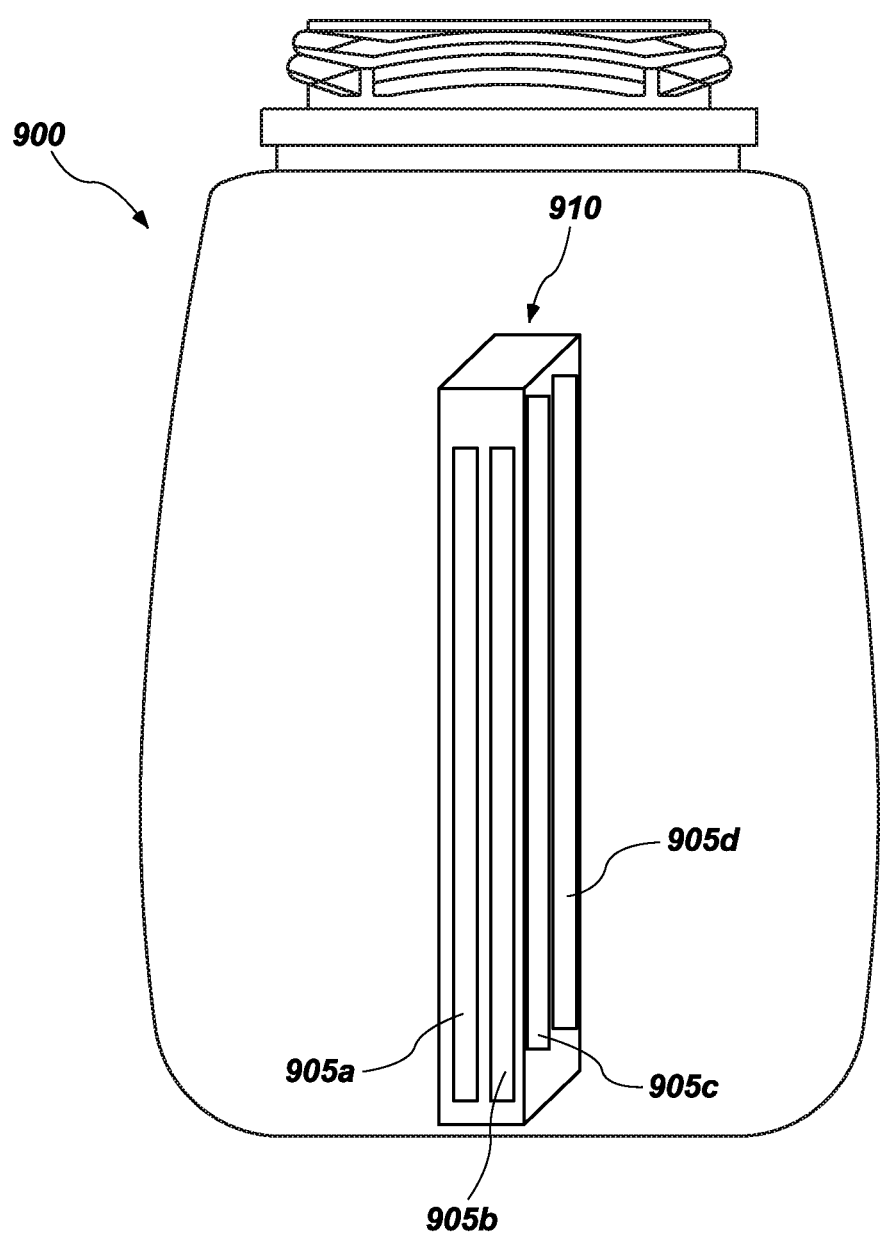
FIG. 9 illustrates an alternative implementation of a fluid collection receptacle in which sensor elements are disposed on a rod disposed within the fluid collection receptacle.

FIG. 9 illustrates an alternative implementation of a fluid collection receptacle 900 in which sensor elements 905a-905d are disposed on a rod 910 disposed within fluid collection receptacle 900. Rod 910 may be formed to rise from a bottom portion of fluid collection receptacle 900 using the same material used for fluid collection receptacle 900 (e.g., plastic). Rod 910 may include sensor elements 905a-905d which are similar in implementation, in this example, to sensor 700 shown in FIG. 7. In FIG. 9, however, rod 910 is shown as being implemented as a square or a rectangular shape, which provides two separate axes for sensing fluid level, as discussed above in FIG. 7. For example, sensor elements 905a and 905b may be formed as a first parallel pair of sensor elements and may be disposed at 90° to sensor elements 905c and 905d, which form a second parallel pair of sensor elements. Such a configuration allows a liquid level within fluid collection receptacle 900 to be sensed regardless of whether fluid collection receptacle 900 is tilted to the left/right or forwards/backwards.

Rod 910 may be hollow along an inside portion of rod 910. In this manner, sensor elements 905a-905d may be disposed on an outside surface of rod 910, an inside surface of rod 910 or may be disposed between an inside and outside surface of rod 910 within the materials that form fluid collection receptacle 900. Regardless, rod 910 may be separated from direct contact with milk contained within fluid collection receptacle 900.

Figure 10:
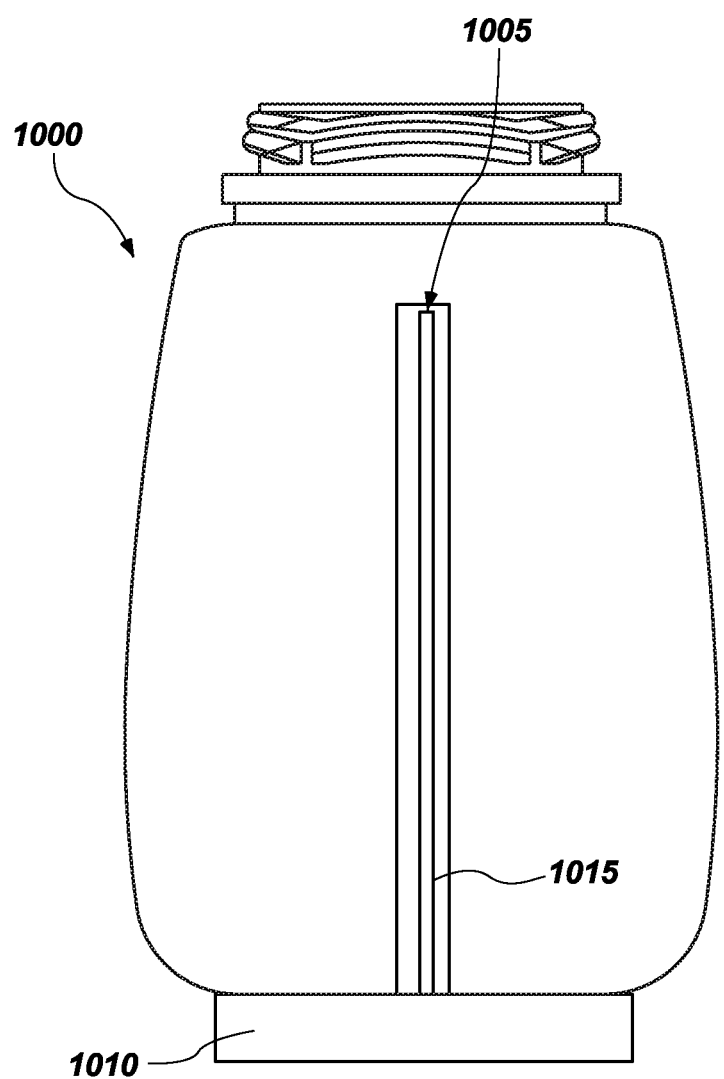
FIG. 10 illustrates a fluid collection receptacle in which a rod may be installed from a bottom portion of the fluid collection receptacle.

FIG. 10 illustrates a fluid collection receptacle 1000 in which a rod 1005 may be installed from a bottom portion 1010 of fluid collection receptacle 1000. Fluid collection receptacle 1000 may include a hole corresponding to the size and shape of rod 1005. Rod 1005 may therefore be inserted into a hole disposed within bottom portion 1010 of fluid collection receptacle 1000 and installed by any connection mechanism between rod 1005 and bottom portion 1010 of fluid collection receptacle 1000. For example, fluid collection receptacle 1000 may include threads into which rod 1005 may be inserted and to which rod 1010 may be connected. Bottom portion 1010 may further include a PCB (printed circuit board) with batteries that may operate the PCB and one or more sensor elements installed in rod 1005. Bottom portion may be threaded onto fluid collection receptacle 1000 and fully sealed for sanitizing.

In one embodiment, a straw 1015 may be installed around rod 1005 to protect milk within fluid collection receptacle 1000 from coming in contact with rod 1005. Straw 1015 may be constructed so as to create a barrier between milk and sensor elements (such as any of the sensor elements disclosed herein) that may be installed on rod 1005 and which cannot be sanitized to a sufficient degree.

Bottom portion 1010 may further include a tilt sensor which identifies when fluid collection receptacle 1000 is tilted away from vertical, or at least far enough away from vertical that the angle of tilt is outside a predetermined threshold of tilt. Bottom portion 1010 may further include a gimbal, or control a gimbal disposed within a breast pump to redirect milk flow during such times as the angle of tilt for fluid collection receptacle 1000 is outside a predetermined level.

Figure 11:
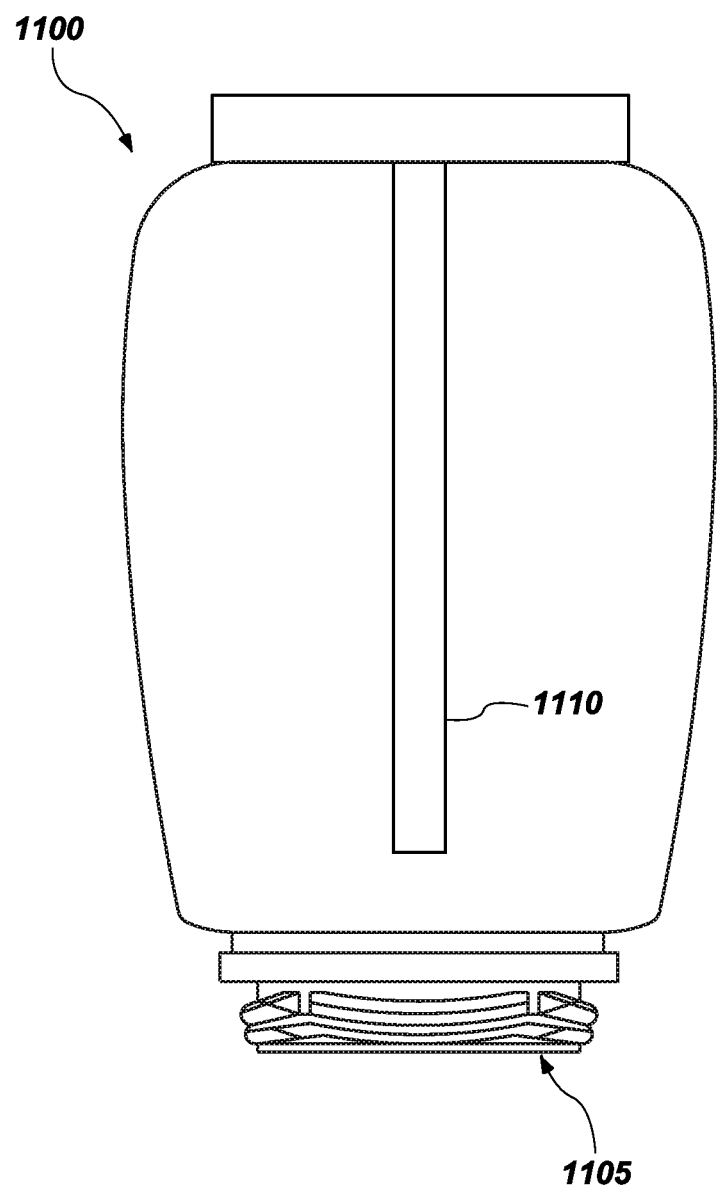
FIG. 11 illustrates a fluid collection receptacle which mates with a sealed housing containing a capacitive or inductive rod which may be installed on a top of the fluid collection receptacle.

FIG. 11 illustrates a fluid collection receptacle 1100 which mates with a sealed housing 1105 containing a capacitive or inductive rod 1110 which may be installed on a top of fluid collection receptacle 1100. In this embodiment, rod 1110 may include sensor elements, such as those disclosed herein, and may be installed at a center of housing 1105 that mates with fluid collection receptacle 1100. Rod 1110 may be sealed within housing 1105 which permits capacitive or inductive coupling to one or more electronic or processing elements. Since housing 1105 and rod 1110 are sealed by a layer of plastic or silicone, housing 1105 and rod 1110 do not directly come into contact with milk contained within fluid collection receptacle 1100. Further, housing 1105 and rod 1110 may be washed by a dishwasher because they are sealed.

In one embodiment, a capacitive sensor element installed on rod 1110 may be implemented as one or more rungs which are disposed side by side along a central ground. One advantage of this implementation is that the capacitive sensor elements may be installed by printing with conductive ink, such as silver ink, which may allow for a better resolution (e.g., accuracy in determining an amount of liquid contained within fluid collection receptacle 1100).

Other measurements for an amount of milk contained within a fluid collection receptacle, such as those fluid collection receptacles disclosed herein. For example, since the specific density of breast milk is relatively consistent between different people (or may be ascertained for each individual), weight may also be an indicator of volume or may be a separate measurement that may be useful. For example, a scale that may be tared for a weight of a fluid collection receptacle (the total weight of the fluid collection receptacle and the milk contained inside minus the predetermined weight of the fluid collection receptacle) may be integrated into a carrying case for the breast pump system. The breast pump system may receive weight information from the scale and volume may be extrapolated and automatically recorded in a memory of a device associated with the breast pump system. In another implementation, a three-dimensional touch system, a force gauge, or a capacitive screen on a smartphone may be used to measure a weight of bottles when a breast pumping session has terminated. The smartphone, for example, may automatically record a weight of the bottle (tared for the weight of the bottle) and extrapolate a total volume of milk contained within the bottle.

Figure 12:
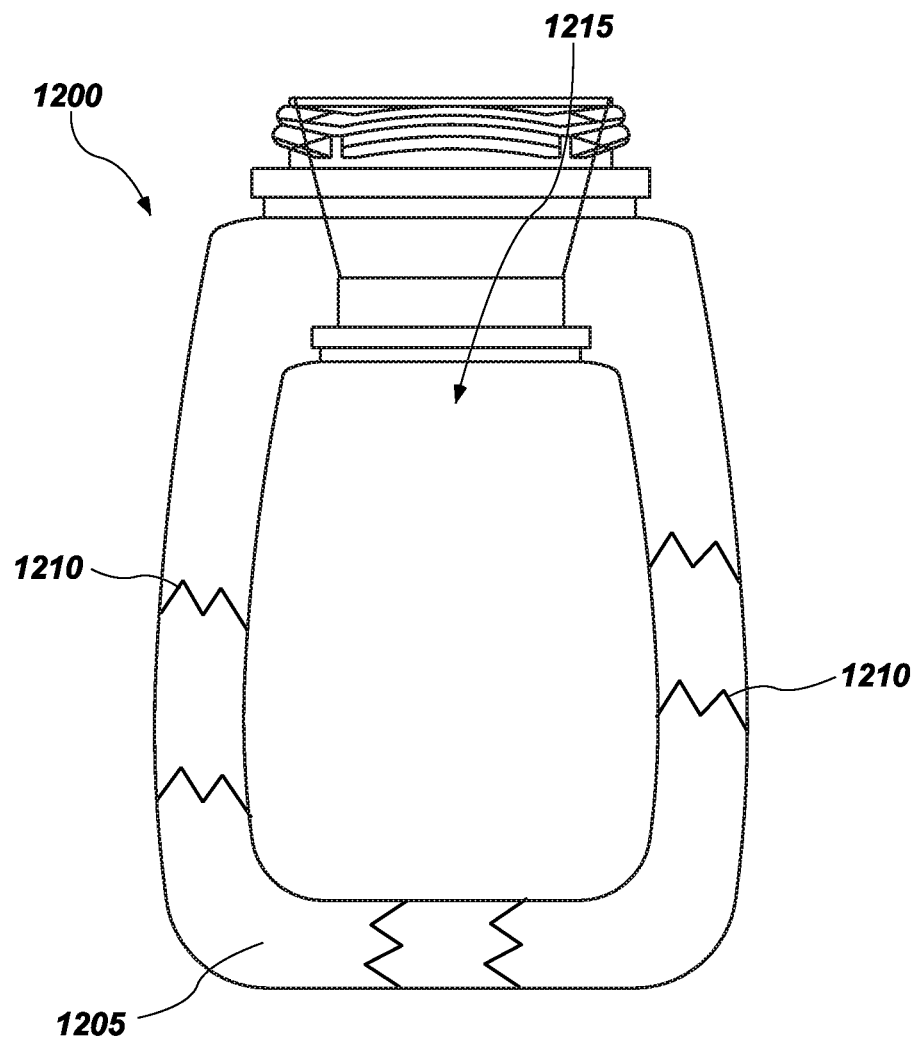
FIG. 12 illustrates a fluid collection receptacle 1200 which contains a housing and one or more strain gauges disposed between the housing and an inner receptacle.

Another implementation, shown in FIG. 12, illustrates a fluid collection receptacle 1200 which contains a housing 1205 and one or more strain gauges 1210 disposed between housing 1205 and an inner receptacle 1215. One advantage of fluid collection receptacle 1200 is that strain gauges may measure the weight of the milk within inner receptacle 1215 while a breast pump is being worn. Further, the inner reservoir may ensure that milk is fully contained within fluid collection receptacle 1200 and isolates any milk that may spill from contacting the user's body or clothes.

Figure 13:
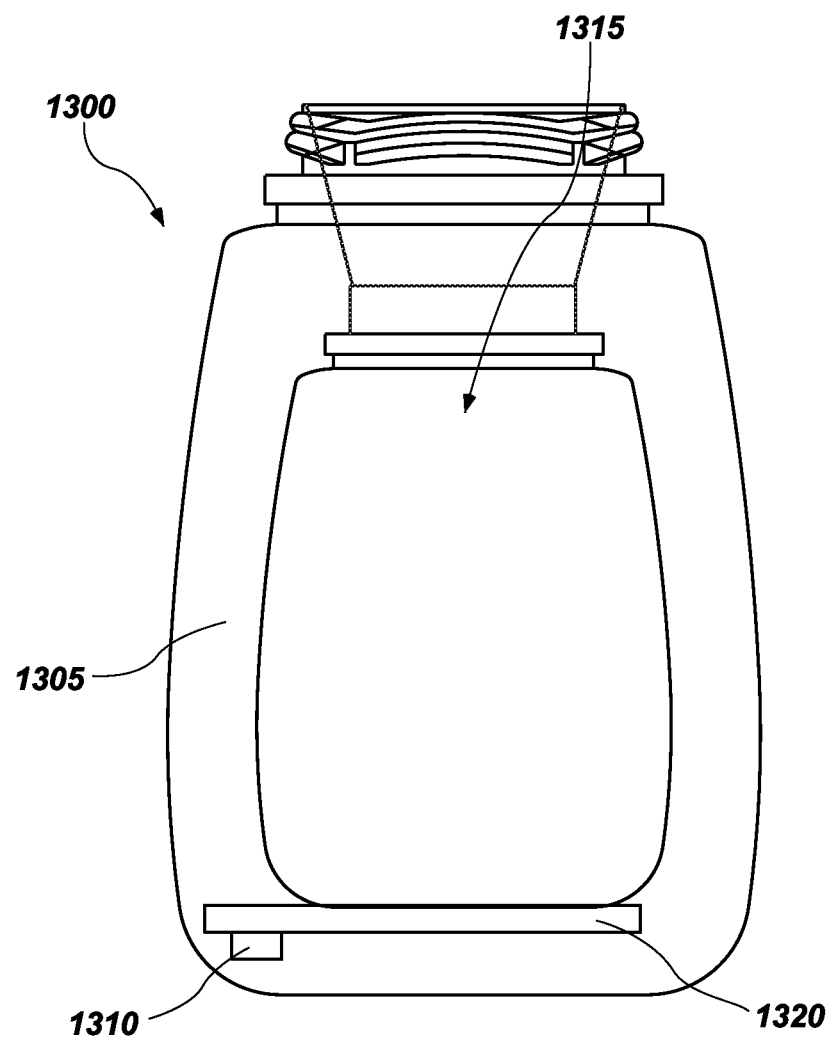
FIG. 13 illustrates a fluid collection receptacle which contains a housing and a strain gauge.

FIG. 13 illustrates a fluid collection receptacle 1300 which contains a housing 1305 and a strain gauge 1310. Strain gauge 1310 may connect housing 1305 to inner receptacle 1315. Inner receptacle 1315 may receive breast milk as it is expressed. As milk aggregates within inner receptacle 1315, strain gauge 1310 may record a weight increase caused by the addition of milk to inner receptacle 1315. In one embodiment, strain gauge 1310 may be disposed under a cantilever 1320 which amplifies the weight of milk in the inner receptacle and provides additional resolution to the weight measurement. In another embodiment, an accelerometer (not shown) may be installed within fluid collection receptacle 1300 to find a force component in the direction of gravity to increase the accuracy of the weight measurement obtained via strain gauge 1310.

Fluid collection receptacle 1300, and the other fluid collection receptacles disclosed herein, may include liquid-level sensors, such as time of flight sensors, capacitive sensors, ultrasonic sensors, optical sensors, and other sensors, coupled to an accelerometer to compensate for tilting while still determining an accurate volume or weight of milk contained within inner receptacle 1315.

Figure 14:
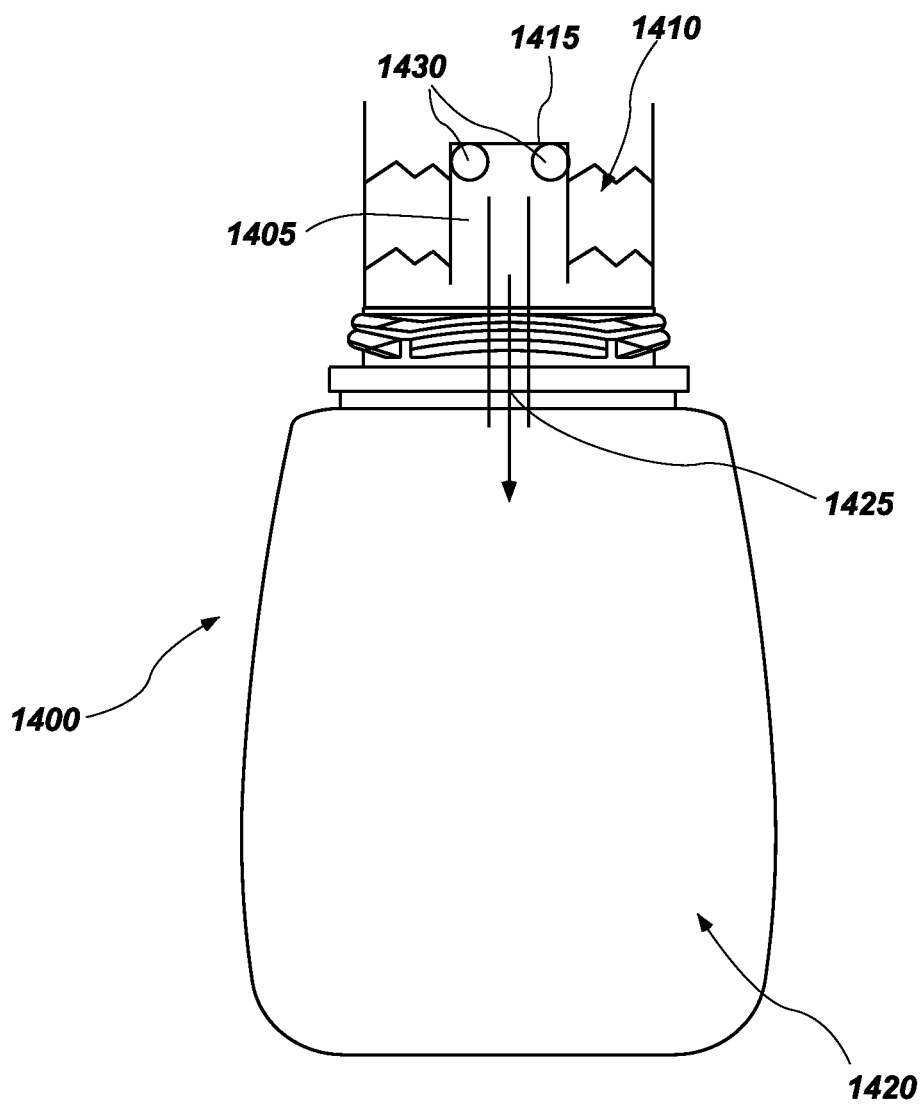
FIG. 14 illustrates a fluid collection receptacle which implements a siphoning system.

FIG. 14 illustrates a fluid collection receptacle 1400 which implements a siphoning system. Fluid collection receptacle 1400 includes one or more siphoning channels 1405 which may allow milk to aggregate to a particular level in a first reservoir 1410 until it reaches a certain level 1415 and is drained into a second reservoir 1420 through a drain 1425 by one or more vacuums 1430 disposed in the one or more siphoning channels 1405. In this manner, as first reservoir 1410 fills with milk, it is subsequently drained into second reservoir 1420. However, since the volume of first reservoir 1410 is known, a mechanism disposed within fluid collection receptacle 1400 (not shown) may count the number of times first reservoir 1410 is drained into second reservoir 1420 and determine a total volume of milk drained into and contained in second reservoir 1420. Other siphoning mechanisms are contemplated. For example, a U-shaped siphon may be implemented instead of the inverted U shaped siphon shown in FIG. 14. Alternatively, a float siphon may be implemented which floats up to a particular level at which a valve is opened and milk in first reservoir 1410 is allowed to drain into second reservoir 1420.

Other systems may be used for determining a fluid level in a fluid collection receptacle. For example, a camera of a smart phone may apply dynamic filters on top of a computer image recognition software for a particular fluid collection receptacle. Image recognition systems may recognize a particular bottle and dynamic filters may be overlaid in real time on top of the bottle displayed on the screen. The filters may be situated or manipulated by a user to demonstrate a volume level in a bottle. Alternatively, the filters may automatically identify a volume level in a bottle and calculate a total volume of milk contained within a fluid collection receptacle.

Another implementation for detecting fluid flow may include a vibration sensor or an optical sensor below a valve in a breast pump which detects fluid flow.

Figure 15A:
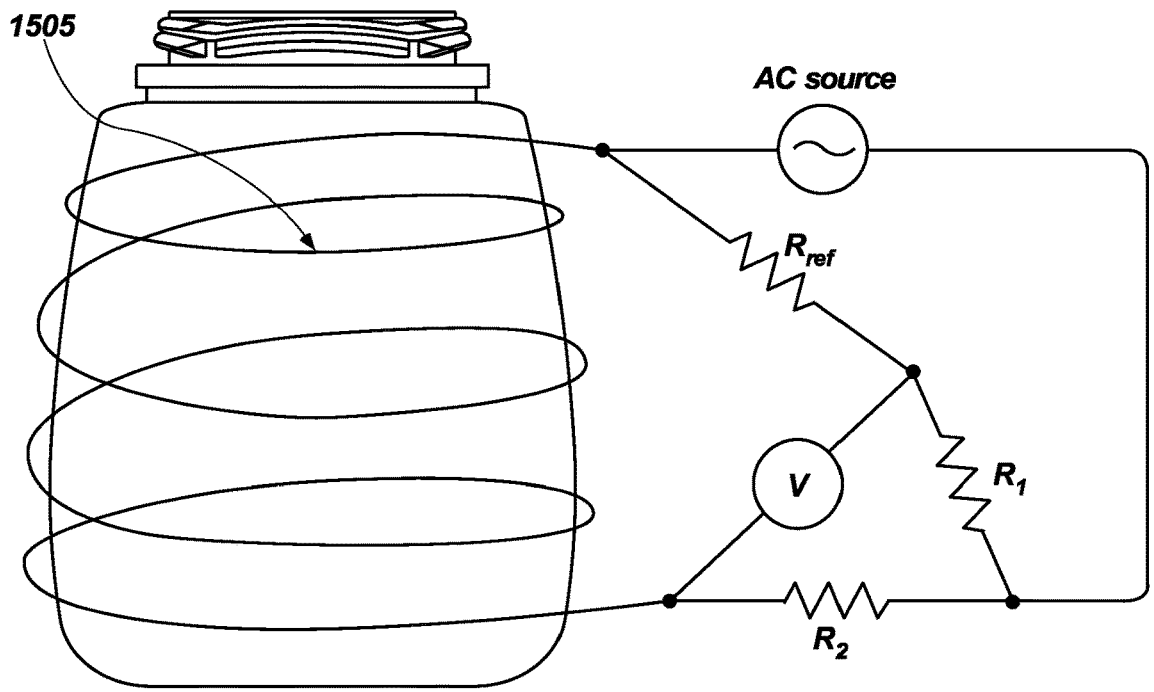
FIG. 15A illustrates an exemplary implementation of a fluid collection receptacle which uses a circuit which includes an inductive coil wrapped circumferentially around the fluid collection receptacle.

Yet another implementation may be based on inductive flow sensing or, in other words, using a copper coil as a flow sensor and to determine a total volume of expressed milk. FIG. 15A illustrates an exemplary implementation of a fluid collection receptacle 1500 which uses an inductive coil 1505 wrapped circumferentially around fluid collection receptacle 1500. Inductive coil 1505 may be installed on an outside surface of fluid collection receptacle 1500, an inside surface of fluid collection receptacle 1500, between an outside surface of fluid collection receptacle 1500 and an inside surface of fluid collection receptacle 1500 within fluid collection receptacle 1500. Alternatively, a sleeve may be installed around fluid collection receptacle 1500 which provides a removable coil disposed around fluid collection receptacle 1500. Inductive coil 1505 is advantageous because it does not come into contact with milk contained within fluid collection receptacle 1500 and measures a total volume of milk inside fluid collection receptacle 1500 regardless of whether or not fluid collection receptacle 1500 is tilted.

As shown in FIG. 15A, a circuit is shown where resistor R1 is equal to resistor to R2 and an AC source is provided to prevent the inductance of the circuit from going to zero. Resistor $R_{ref}$ may be tuned to resistor $R_L$, which corresponds to the resistance of inductive coil 1505 when there is no milk within fluid collection receptacle 1500, such that the voltage V of the circuit is zero. As milk fills fluid collection receptacle 1500, voltage V changes. This change in voltage V may be used to calculate a total amount of milk contained within fluid collection receptacle 1500.

Figure 15B:
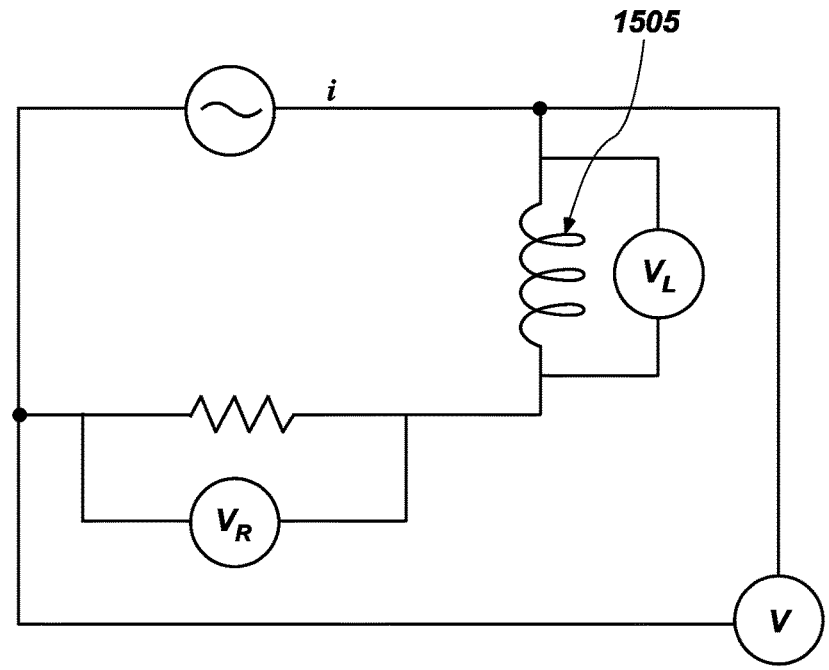
FIG. 15b illustrates another exemplary circuit which may be used to identify an absolute voltage through an inductor coil.

In FIG. 15B, another exemplary circuit may be used which may be used to identify an absolute voltage through an inductor coil. $V_L$: may be a voltage across inductive coil 1505 while voltage $V_R$ may be a voltage across the entire system (e.g., based on the total resistance across the system). As shown in FIG. 15B, the system may further include an AC source. Unfortunately, a total voltage V cannot be determined by a volt meter because the total voltage of the circuit has components of both $V_R$ and $V_L$. However, because it is known that $V_L = -L\, di/dt$, $V_R$ and $V_L$ may be distinguished because $V_R$ and $V_L$ are 90° out of phase with each other. Because of this, an absolute voltage $V_L$ may be measured without a need to balance or tune inductive coil 1505 to resistor $R_{ref}$, as discussed above with respect to FIG. 15A.

Initially, however, there are some complications in adjusting for appropriate sensitivity for inductive coil 1505 and achieving the appropriate resolution for accurately determining an amount of milk within fluid collection receptacle 1500. Once $V_L$ is accurately identified, $V_L$ may be amplified enough to measure a difference in the total inductance due to air and due to milk according to the following equation:

$$L = N^2 * \mu A / l$$

Where L is the total inductance of the circuit, N is the total number of coils wrapped around fluid collection receptacle 1500, µ is a magnetic constant, A is a cross sectional area of fluid collection receptacle 1500, and l is a total length of inductive coil 1505. It should also be noted that the magnetic constant µ of milk is not equal to the magnetic constant µ of air. Other implementations are possible that are based on the phase between two different reference voltages. For example, reactance, and the ESR (equivalent series resistance) of a coil may be used to determine self-inductance with a relatively high accuracy.

Figure 16:
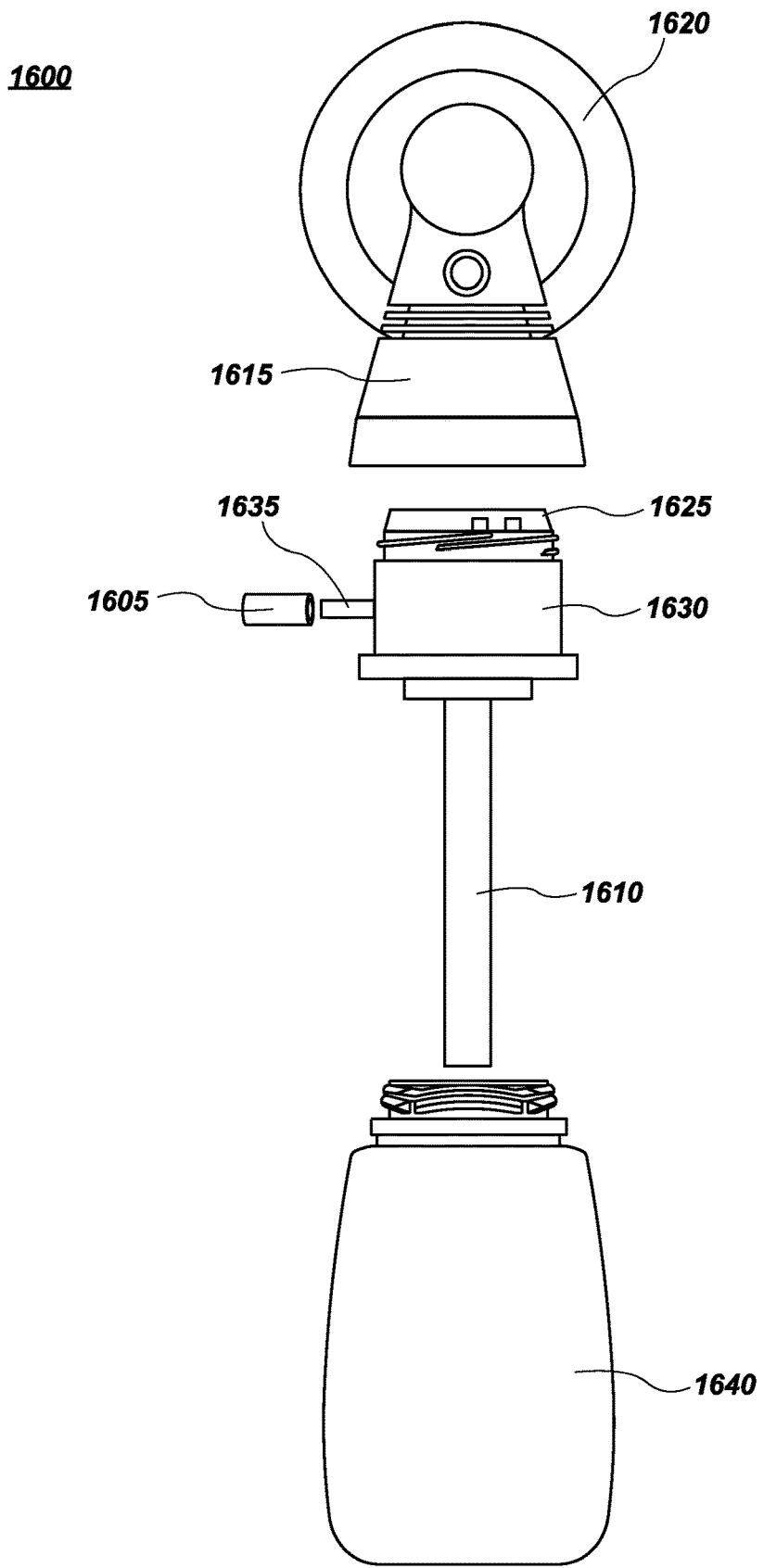
FIG. 16 illustrates an exploded view of a fluid collection receptacle that implements a pressure sensor with a rigid tube to track pressure changes and determine a volume of fluid within the fluid collection receptacle.

FIG. 16 includes a fluid collection receptacle 1600 that implements a pressure sensor 1605 with a rigid tube 1610 to track pressure changes and determine a volume of fluid within fluid collection receptacle 1600. Pressure sensor 1605 may detect air pressure inside rigid tube 1610, which may be enclosed by fluid within fluid collection receptacle 1600. As liquid fills rigid tube 1610, air pressure increases which, in turn, reflects an increase in liquid volume within fluid collection receptacle 1600. Based on the increase of air pressure inside fluid collection receptacle 1600, a pressure sensor 1605 may be used to determine a corresponding volume for an amount of pressure within fluid collection receptacle 1600. Rigid tube 1610 may be positioned at an approximate midpoint or center of fluid collection receptacle 1600 to minimize pressure changes caused by the amount of tilt for fluid collection receptacle 1600.

As shown in FIG. 16, pressure sensor 1605 and rigid tube 1610 may be in fluid communication such that air that is pushed into rigid tube 1610 is also pushed through port 1635 into pressure sensor 1605. However, an air permeable liquid proof seal may be implemented to ensure that a liquid within rigid tube 1610 cannot come into contact with pressure sensor 1605 or other electronics within fluid collection receptacle 1600. In other words, rigid tube 1610 may be connected to port 1635 through adapter 1630. Fluid collection receptacle 1600 may further include a breast pump manifold 1615 which may contain electronics, sensors, a computer processor, antennas, transmitters, provide vacuum suction, and attach to adapter 1630 by an air tight connection. Breast pump manifold 1615 may further include removable breast flange 1620 for interfacing with a breast to stimulate milk production.

Adapter 1630 may be fitted with a valve 1625 which may maintain vacuum pressure within manifold 1615 while also allowing a liquid, such as milk, to fall through valve 1625 and into bottle 1640. As previously discussed, as the liquid accumulates in bottle 1640 and displaces air in bottle 1640, the liquid will enter into rigid tube 1610. As the liquid rises in tube 1610, air within tube 1610 may be compressed, increasing air pressure within tube 1610. Pressure sensor 1605 may detect this increased pressure and provide this information wirelessly or with a wired connection, to a processor which may then determine a volume of liquid within bottle 1640 based on the pressure detected from pressure sensor 1605 and the known volume of bottle 1640. Pressure sensor 1605 may be a piezoresistive silicon pressure sensor with a digital output, or may be implemented as another pressure sensor known in the art.

Figure 17:
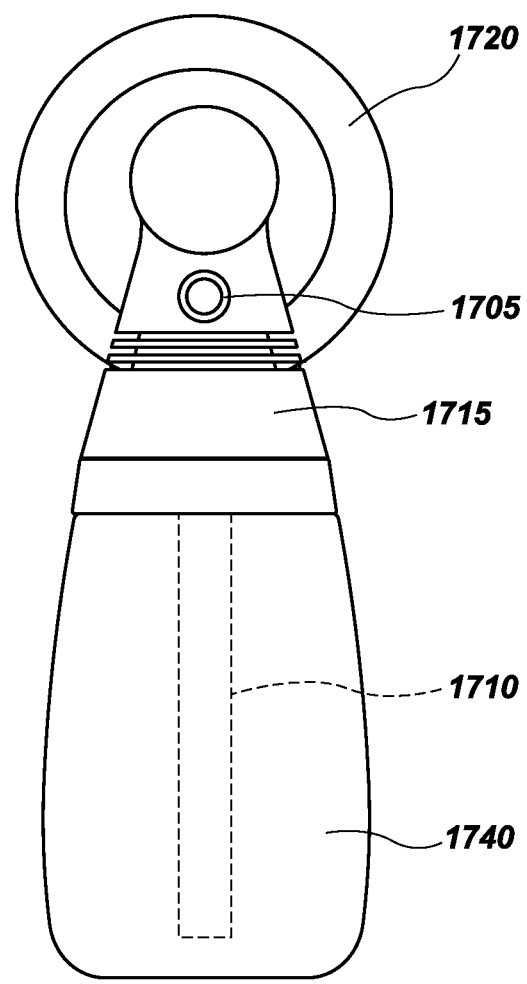
FIG. 17 illustrates an assembled view of the fluid collection receptacle shown in FIG. 16.

FIG. 17 illustrates an assembled view of the fluid collection receptacle 1600 shown in FIG. 16. Fluid collection receptacle 1700 implements a pressure sensor 1705 with a rigid tube 1710 to track pressure changes and determine a volume of fluid within fluid collection receptacle 1700. Pressure sensor 1705 may detect air pressure inside rigid tube 1710, which may be enclosed by fluid within fluid collection receptacle 1700. As liquid fills rigid tube 1710, air pressure increases which, in turn, reflects an increase in liquid volume within fluid collection receptacle 1700. Based on the increase of air pressure inside fluid collection receptacle 1700, a pressure sensor 1705 may be used to determine a corresponding volume for an amount of pressure within fluid collection receptacle 1700. Rigid tube 1710 may be positioned at an approximate midpoint or center of fluid collection receptacle 1700 to minimize pressure changes caused by the amount of tilt for fluid collection receptacle 1700.

As shown in FIG. 17, pressure sensor 1705 and rigid tube 1710 may be in fluid communication such that air that is pushed into rigid tube 1710 is also pushed through port 1735 into pressure sensor 1705. However, an air permeable liquid proof seal may be implemented to ensure that a liquid within rigid tube 1710 cannot come into contact with pressure sensor 1705 or other electronics within fluid collection receptacle 1700. In other words, rigid tube 1710 may be connected to port 1735 through adapter 1730. Fluid collection receptacle 1600 may further include a breast pump manifold 1715 which may contain electronics, sensors, a computer processor, antennas, transmitters, provide vacuum suction, and attach to adapter 1730 by an air tight connection. Breast pump manifold 1715 may further include removable breast flange 1720 for interfacing with a breast to stimulate milk production.

Adapter 1730 may be installed on bottle 1740 by mating threads disposed on adapter 1730 and bottle 1740. Adapter 1730 may also attach to a valve 1725 which may be disposed in manifold 1715 by mating threads on adapter 1730 and an inside of manifold 1715. Adapter 1730 essentially provides a connection between manifold 1715 and bottle 1740 and a connection between rigid tube 1710 and port 1735 for pressure sensor 1705.

As previously discussed, adapter 1730 may be fitted with a valve 1725. In this configuration, valve 1725 may maintain vacuum pressure within manifold 1715 while also allowing a liquid, such as milk, to fall through valve 1725 and into bottle 1740. As previously discussed, as the liquid accumulates in bottle 1740 and displaces air in bottle 1740, the liquid will enter into rigid tube 1710. As the liquid rises in tube 1710, air within tube 1710 may be compressed, increasing air pressure within tube 1710. Pressure sensor 1705 may detect this increased pressure and provide this information wirelessly or with a wired connection, to a processor which may then determine a volume of liquid within bottle 1740 based on the pressure detected from pressure sensor 1705 and the known volume of bottle 1740. Pressure sensor 1705 may be a piezoresistive silicon pressure sensor with a digital output, or may be implemented as another pressure sensor known in the art.

Figure 18:
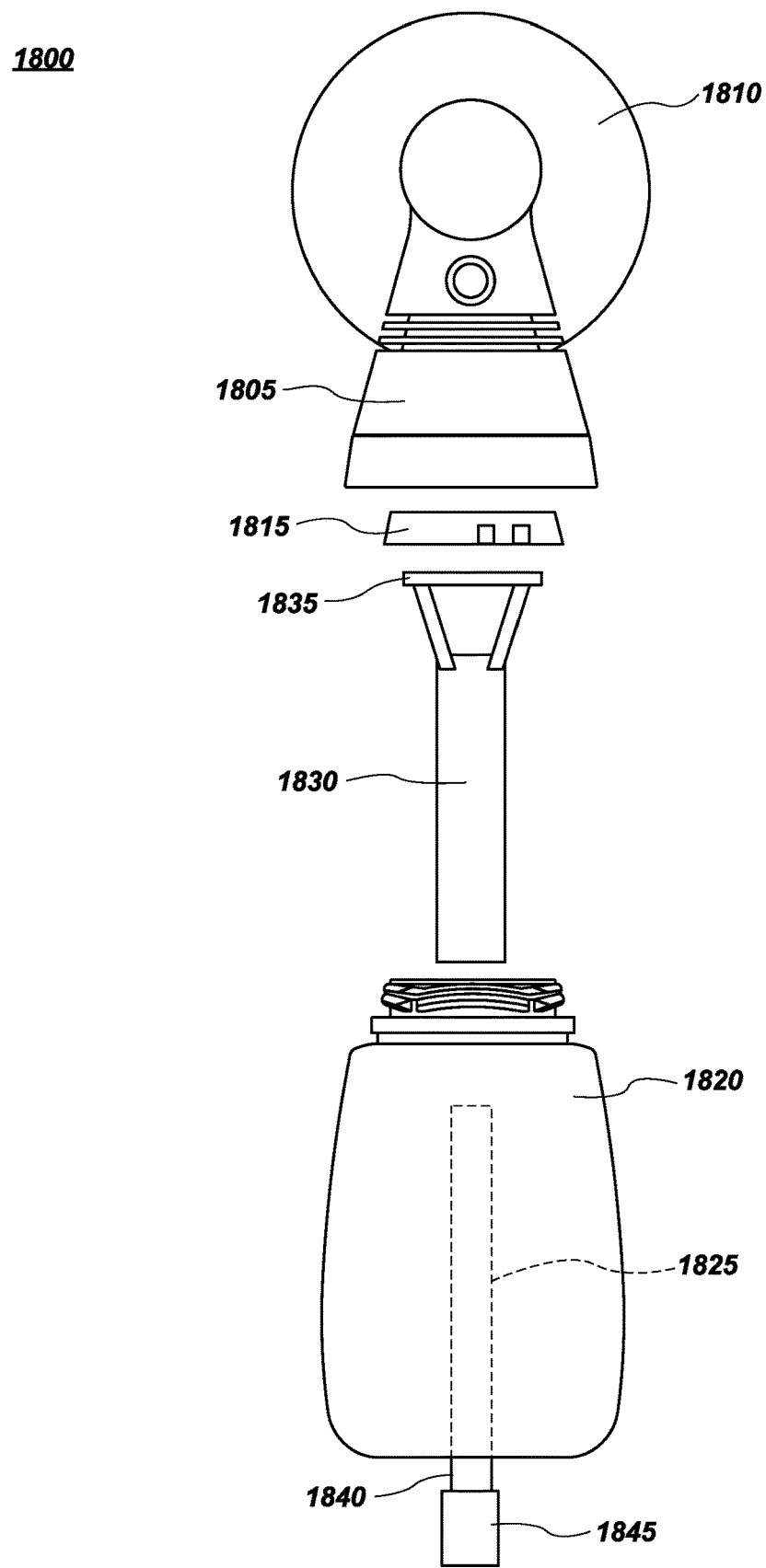
FIG. 18 illustrates an exploded view of another embodiment of a fluid collection receptacle that implements a pressure sensor with a rigid tube to track pressure changes and determine a volume of a fluid within the fluid collection receptacle.

FIG. 18 illustrates an exploded view of another embodiment of a fluid collection receptacle 1800 that implements a pressure sensor 1845 with rigid tubes 1825 and 1830 to track pressure changes and determine a volume of a fluid within fluid collection receptacle 1800. Pressure sensor 1845 may detect air pressure inside rigid tube 1825, which may be enclosed by fluid within fluid collection receptacle 1800. As liquid fills rigid tube 1830, air pressure increases which, in turn, reflects an increase in liquid volume within fluid collection receptacle 1800. Based on the increase of air pressure inside fluid collection receptacle 1800, a pressure sensor 1805 may be used to determine a corresponding volume for an amount of pressure within fluid collection receptacle 1800. Rigid tube 1810 may be positioned at an approximate midpoint or center of fluid collection receptacle 1800 to minimize pressure changes caused by the amount of tilt for fluid collection receptacle 1800.

As shown in FIG. 18, fluid collection receptacle 1800 includes a manifold 1805 which further provides a flange 1810 for interfacing with a breast for stimulating milk production. Vacuum pressure may be applied via manifold 1805 and flange 1810 to a nipple to cause the nipple to express milk. Fluid collection receptacle 1800 may further include a valve 1815 which maintains vacuum within manifold 1805 while also allowing a liquid, such as milk, to pass through valve 1815 into bottle 1820. Valve 1815 may connect to bottle 1820 by mating threads or other fasteners disposed in valve 1815 and bottle 1820. Valve 1815, may also connect to manifold 1805 by a threaded connection or by other fasteners known in the art.

In FIG. 18, fluid collection receptacle 1700 provides rigid tube 1830, which may also be referred to as a second rigid tube or an outside rigid tube. Second rigid tube 1830 may include a valve interface 1835 which may selectively connect or interface second rigid tube 1830 to valve 1815 such that an opening in second rigid tube 1830 may be disposed more closely to a bottom of bottle 1820 than a top of bottle 1820. Further, second rigid tube 1830 may be closed on one end and have a greater diameter than rigid tube 1825, which is disposed in a bottom of bottle 1820. Rigid tube 1825 may be fashioned as integral to bottle 1820 and connect to port 1840 which provides a connection point and sensor point for pressure sensor 1845.

Figure 19:
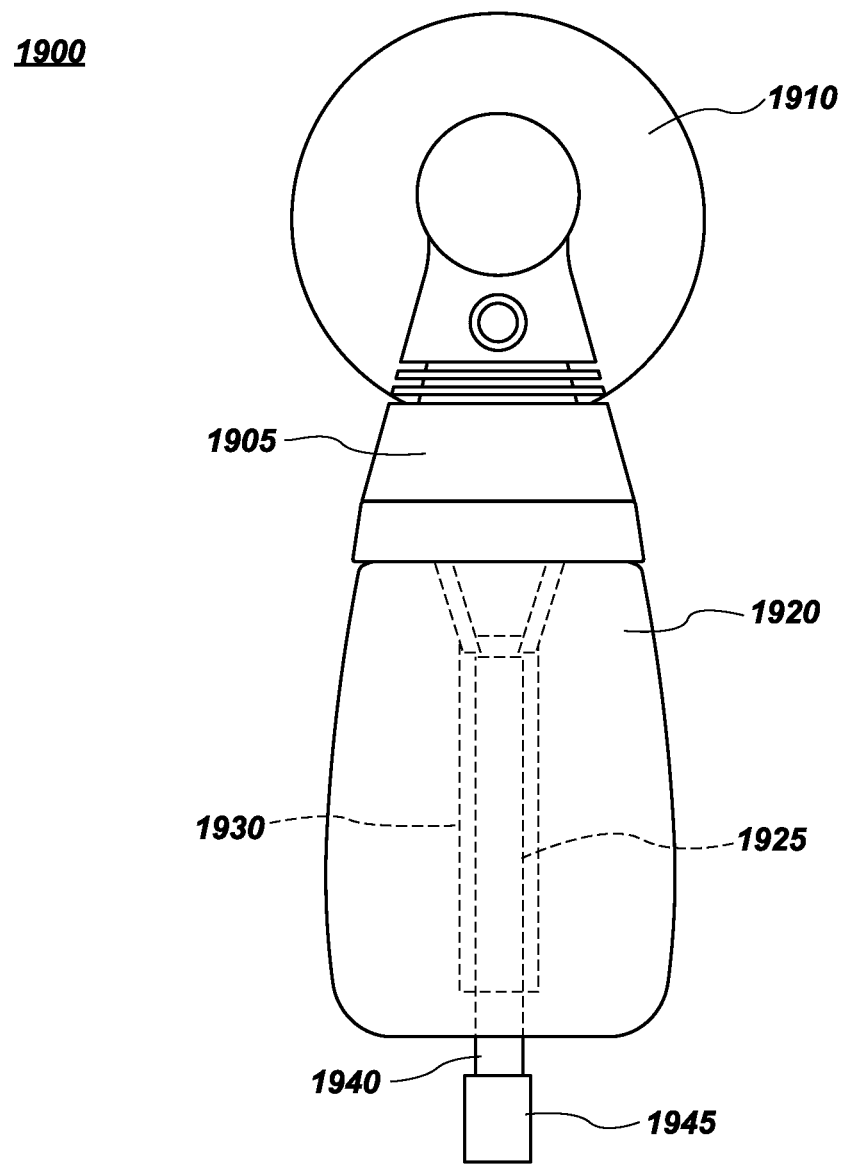
FIG. 19 illustrates an assembled view of the fluid collection receptacle shown in FIG. 18.

FIG. 19 illustrates an assembled view of the fluid collection receptacle 1800 shown in FIG. 18 as fluid collection receptacle 1900. Fluid collection receptacle 1900 may include a manifold 1905, a flange 1910, a valve 1915, a bottle 1920 with integral rigid tube 1925, a second rigid tube 1930 with a valve interface 1935, a port 1940, and a pressure sensor 1945, each of which are similar in implementation and description to corresponding parts shown in FIG. 18 and discussed above.

A shown in FIG. 19, manifold 1905 may connect to valve 1915 and also connect, by threaded connection, or other fasteners known in the art, to bottle 1920 such that valve 1915 is disposed on a top of bottle 1920 or within manifold 1905. Valve 1915 may further connect to or interface with second rigid tube 1935 such that second rigid rube 1935 is secured over and around rigid tube 1925 within bottle 1920. Rigid tube 1925 may provide fluid communication between an inside of bottle 1920 and an outside of bottle 1920 through port 1940 such that pressure sensor 1945 may be exposed to pressure changes within bottle 1920.

In operation, as a liquid, such as milk, is received into manifold 1905 and falls through valve 1915, the liquid may collect within bottle 1920. As a liquid level rises in bottle 1920 from accumulating liquid, the liquid may enter second rigid tube 1925 and begin to push air into rigid tube 1925. The air may become increasingly pressurized as additional liquid is received into bottle 1920 and pushes further and further into second rigid tube 1925. This increasing pressurization reflects an increase in liquid volume within fluid collection receptacle 1900. Based on the increase of air pressure inside fluid collection receptacle 1900, information derived from pressure sensor 1945 may be used to determine a corresponding volume for an amount of pressure within fluid collection receptacle 1900.

The foregoing description has been presented for purposes of illustration. It is not exhaustive and does not limit the invention to the precise forms or embodiments disclosed. Modifications and adaptations will be apparent to those skilled in the art from consideration of the specification and practice of the disclosed embodiments. For example, components described herein may be removed and other components added without departing from the scope or spirit of the embodiments disclosed herein or the appended claims.

Other embodiments will be apparent to those skilled in the art from consideration of the specification and practice of the disclosure disclosed herein. It is intended that the specification and examples be considered as exemplary only, with a true scope and spirit of the invention being indicated by the following claims.

What is claimed is:

1. A fluid collection receptacle comprising a pressure sensor connected to a bottle which detects air pressure in the bottle as the bottle is filled with liquid and an integral rigid tube disposed within the bottle that is integral to the bottle and connected to a port, the pressure sensor also being connected to the port, wherein a second rigid tube is disposed over and around the integral rigid tube and includes a valve interface interfacing a valve disposed within a breast pump manifold and wherein the breast pump manifold is connected to a top portion of the bottle.

2. The fluid collection receptacle of claim 1, wherein the valve is a one-way valve.

3. The fluid collection receptacle of claim 2, wherein the valve selectively allows liquid to fall through the valve and collect within the bottle.

4. The fluid collection receptacle of claim 1, wherein the integral rigid tube and the port are connected with an adapter.

5. The fluid collection receptacle of claim 4, wherein the adapter connects the bottle to the breast pump manifold.

6. The fluid collection receptacle of claim 5, wherein the valve connects to the adapter.

7. The fluid collection receptacle of claim 6, wherein the valve selectively allows the liquid to fall into the bottle.

8. The fluid collection receptacle of claim 4, wherein the integral rigid tube is disposed at an approximate center of the bottle when the bottle is attached to the adapter.

9. The fluid collection receptacle of claim 1, wherein an air permeable liquid proof seal is disposed between the pressure sensor and the integral rigid tube.

10. The fluid collection receptacle of claim 1, wherein air pressure information detected by the pressure sensor is wirelessly transmittable to a processor.

11. The fluid collection receptacle of claim 1, wherein air pressure information detected by the pressure sensor is transmittable to a processor via a wire.

12. The fluid collection receptacle of claim 1, wherein the air pressure sensor is a pressurized sensor.

13. The fluid collection receptacle of claim 1, where in the second rigid tube has a diameter greater than a diameter of the integral rigid tube.

\* \* \* \* \*